United States Patent
Yamaguchi et al.

(10) Patent No.: US 9,238,128 B2
(45) Date of Patent: Jan. 19, 2016

(54) NEEDLELESS CONNECTOR

(71) Applicant: NIPRO CORPORATION, Osaka-shi, Osaka (JP)

(72) Inventors: Takeshi Yamaguchi, Osaka (JP); Tomohiro Uchimura, Osaka (JP); Kohzo Ishikura, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 14/366,387

(22) PCT Filed: Dec. 27, 2012

(86) PCT No.: PCT/JP2012/008371
§ 371 (c)(1),
(2) Date: Jun. 18, 2014

(87) PCT Pub. No.: WO2013/099261
PCT Pub. Date: Jul. 4, 2013

(65) Prior Publication Data
US 2014/0316350 A1  Oct. 23, 2014

(30) Foreign Application Priority Data
Dec. 27, 2011 (JP) .................. 2011-284921

(51) Int. Cl.
*A61M 39/26* (2006.01)
*A61M 39/06* (2006.01)
(Continued)

(52) U.S. Cl.
CPC ............... *A61M 39/06* (2013.01); *A61M 39/26* (2013.01); *A61M 2039/066* (2013.01);
(Continued)

(58) Field of Classification Search
CPC ............... A61M 39/06; A61M 39/26; A61M 2039/0633; A61M 2039/064; A61M 2039/066; A61M 2039/2406; A61M 2039/2426; A61M 2039/246; A61M 2039/261
See application file for complete search history.

(56) References Cited

U.S. PATENT DOCUMENTS 5,509,433 A  4/1996  Paradis
5,730,418 A  3/1998  Feith et al.
(Continued)

FOREIGN PATENT DOCUMENTS

JP  A-8-168535  7/1996
JP  A-2004-275472  10/2004
(Continued)

OTHER PUBLICATIONS

International Search Report issued in International Application No. PCT/JP2012/008371 mailed Mar. 12, 2013.
(Continued)

*Primary Examiner* — Nathan R Price
(74) *Attorney, Agent, or Firm* — Oliff PLC (57) ABSTRACT

A bottomed, tubular hollow elastic body that opens toward an outlet side of a drug solution flow path is accommodated and arranged in an accommodation part formed in a housing, and a middle protrusion is provided protruding toward an inlet side of the drug solution flow path from a center part of a bottom wall of the hollow elastic body. Insertion of a male luer causes the bottom wall of the hollow elastic body to be elastically deformed so as to enter inside a peripheral wall, increasing the volume of the drug solution flow path, which is formed between an outer surface of the hollow elastic body and an inner surface of the accommodation part. Removing the male luer and canceling the elastic deformation of the hollow elastic body causes the volume of the drug solution flow path to be reduced.

13 Claims, 9 Drawing Sheets

(51) Int. Cl.
*A61M 39/24* (2006.01)
*A61M 39/10* (2006.01)

(52) U.S. Cl.
CPC .............. *A61M 2039/0633* (2013.01); *A61M 2039/1072* (2013.01); *A61M 2039/2406* (2013.01); *A61M 2039/246* (2013.01); *A61M 2039/2426* (2013.01); *A61M 2039/261* (2013.01); *A61M 2039/263* (2013.01)

(56) References Cited

U.S. PATENT DOCUMENTS

| | | | | |
|---|---|---|---|---|
| 5,806,831 | A | * | 9/1998 | Paradis ................ 251/149.1 |
| 6,050,978 | A | * | 4/2000 | Orr et al. ................ 604/249 |
| 6,871,838 | B2 | | 3/2005 | Raines et al. |
| 2008/0172003 | A1 | | 7/2008 | Plishka et al. |

FOREIGN PATENT DOCUMENTS

| | | |
|---|---|---|
| JP | A-2006-515220 | 5/2006 |
| WO | 98/26835 A1 | 6/1998 |
| WO | 99/24090 A1 | 5/1999 |
| WO | 01/07102 A2 | 2/2001 |
| WO | 03/018104 A2 | 3/2003 |
| WO | 2008/022040 A1 | 2/2008 |

OTHER PUBLICATIONS

Jul. 1, 2014 International Preliminary Report on Patentability issued in International Application No. PCT/JP2012/008371.

May 4, 2015 Extended European Search Report issued in European Patent Application No. 12862179.4.

* cited by examiner

NEEDLELESS CONNECTOR

TECHNICAL FIELD

The present invention relates to a needleless connector used for fluid flow paths such as transfusion routes or the like in the medical field, making it possible to connect a male luer provided on a syringe or the like to the fluid flow path.

BACKGROUND ART

With fluid flow paths for which transfusion, blood transfusion or the like is performed in the medical field, to make it possible to connect and disconnect a syringe, transfusion bag or the like, a needleless connector is sometimes used. This needleless connector is constituted provided with a drug solution flow path inlet and outlet at one side and the other side of the lengthwise direction of the housing, and with an elastic valve body equipped with a slit at the inlet attached. The outlet of the drug solution flow path can be connected with a catheter, and by a catheter inserted in a blood vessel being connected with the drug solution flow path outlet, the drug solution flow path and the blood vessel are in communication.

Also, the drug solution flow path is switched from a blocked state to a communicating state by opening a slit by the elastic valve body being elastically deformed by the male luer inserted from the inlet of the drug solution flow path. Drug solution administration to the patient is performed by having a drug solution flow into the needless connector interior from a syringe or the like connected to the male luer in this kind of communicating state with the drug solution flow path. When drug solution administration is completed, the male luer is removed from the housing, and by the slit of the elastic valve body closing, the drug solution flow path is blocked by the elastic valve body, and the male luer is disconnected from the drug solution flow path connected to the blood vessel or the like.

However, with the needleless connector, when removing the male luer from the slit, there is the risk that blood will enter from the blood vessel to the catheter connected to that drug solution flow path (backflow), and that blood coagulation will occur. In light of that, there is demand for a needleless connector for which it is possible to prevent backflow of blood when removing the male luer from the slit.

In light of that, with PCT Japanese Translation Patent Publication No. JP-A-2006-515220 (Patent Document 1) and the like, a hollow elastic body (piston) is arranged in the accommodation part of the housing, and by the hollow elastic body being pressed by a male luer such as of a syringe or the like, compression deformation occurs in the axial direction on the tube shaped piston wall, and the drug solution flow path is switched to the communicating state. Then, by the male luer being removed, the deformation of the hollow elastic body is cancelled, the drug solution flow path is switched to the blocked state, and backflow of blood is prevented.

However, with the structure of Patent Document 1, there is the problem that with things such as blocking by the piston wall for which the lower channel has deformed or the like, switching to the communicating state for the drug solution flow cannot be realized with sufficient reliability.

Furthermore, the tube shaped piston wall is compressed in the axial direction by the pressing force of the male luer, but when the piston wall is made thin and deforms easily, it is difficult to obtain sufficient shape restoring force based on the elasticity of the item itself, and an auxiliary spring such as a coil spring or the like is needed. Meanwhile, when the piston wall is made thick to obtain sufficient shape restoring force by the elasticity of the piston wall itself, there is the risk of problems such as it being difficult for compression deformation to occur with the piston wall, making it difficult to do the operation of switching the drug solution flow path to the communicating state, or the piston wall overall deforming so as to bulge to the outer circumference side, blocking the drug solution flow path or the like.

As noted in FIG. 7 and FIG. 8 of U.S. Pat. No. 5,730,418 (Patent Document 2), it is also conceivable to stabilize the hollow elastic body deformation mode by doing something like making the part to be deformed by pressing by the male luer at the hollow elastic body a bellows shape in advance or the like. However, in this case as well, due to the pressure fluctuation that accompanies the volume change of the drug solution flow path, the problem of blood backflow before blocking of the drug solution flow path is not eliminated. Furthermore, since the bellows part of the hollow elastic body undergoes general compression deformation in the axial direction, it is difficult to realize both ease of deformation and sufficient shape restorability, and it was difficult to stably and quickly perform switching between the drug solution flow path communicating state and the blocked state.

BACKGROUND ART DOCUMENTS

Patent Documents

Patent Document 1: JP-A-2006-515220
Patent Document 2: U.S. Pat. No. 5,730,418

SUMMARY OF THE INVENTION

Problem the Invention Attempts to Solve

Here, the present invention was created with the circumstances described above in the background, and the problem it is to solve is to provide a needleless connector of a novel structure that is able to realize both stable administration of a drug solution or the like and prevention of backflow of blood or the like by stably and quickly switching between communication and blocking of the drug solution flow path using a simple structure.

Means for Solving the Problem

Specifically, a first mode of the present invention provides a needleless connector wherein an inlet and an outlet of a drug solution flow path are respectively provided at one side and another side of a lengthwise direction of a housing, and an elastic valve body having a slit is attached to the inlet of the drug solution flow path of the housing such that the drug solution flow path is switched from a blocked state to a communicating state by opening the slit by the elastic valve body being deformed by means of insertion of a male luer from the inlet of the drug solution flow path, the needleless connector being characterized in that: a hollow elastic body having a tube shape with a bottom that opens toward an outlet side of the drug solution flow path is accommodated and arranged in an accommodation part formed on the housing; a middle protrusion is provided protruding toward an inlet side of the drug solution flow path from a center part of a bottom wall of the hollow elastic body; by means of insertion of the male luer, the bottom wall of the hollow elastic body undergoes elastic deformation so as to enter inside a peripheral wall of the hollow elastic body, and a volume of the drug solution flow path formed between an outer surface of the hollow elastic body and an inner surface of the accommodation part is increased; and by means of removal of the male luer, the elastic deformation of the hollow elastic body is cancelled, and the volume of the drug solution flow path is reduced.

With the needleless connector constituted according to the first mode of the present invention, the hollow elastic body accommodated and arranged in the accommodation part is made to undergo elastic deformation so as to have the bottom wall pushed into the inner circumference side of the peripheral wall by the push-in force of the male luer applied to the distal end of the middle protrusion. Because of that, it is possible to stably increase the volume of the drug solution flow path extending between the housing and the hollow elastic body by the insertion of the male luer, and when the male luer is removed, there is a decrease in the volume of the drug solution flow path by the shape restoration of the hollow elastic body. As a result, since positive pressure acts inside the drug solution flow path, it is possible to effectively prevent the backflow of blood from the blood vessel to the catheter connected to the drug solution flow path.

In fact, since the hollow elastic body is deformed such that the bottom wall enters the inner circumference side of the peripheral wall, injection of the drug solution to the outlet side through the drug solution flow path is realized stably without blocking of the drug solution flow path formed between the housing and the hollow elastic body due to the elastically deformed hollow elastic body.

A second mode of the present invention provides the needleless connector according to the first mode, wherein the hollow elastic body is an integrally molded component that is integrally molded using an elastic material including the middle protrusion.

With the second mode, since the hollow elastic body is an integrally molded component including the middle protrusion, the structure is made simpler by reducing the number of parts. As a result, it is possible to realize improvements in manufacturing ease and operating stability.

A third mode of the present invention provides the needleless connector according to the first or second mode, wherein a lid part that covers an opening of the hollow elastic body is provided, a deformation allowance space is formed between the lid part and the hollow elastic body, and an opening passage is formed on the lid part so as to put the deformation allowance space in communication with an external space.

With the third mode, infiltration of foreign matter and the like is avoided by the opening of the hollow elastic body being covered by the lid part. In fact, a deformation allowance space is provided between the lid part and the hollow elastic body, and the deformation allowance space is in communication with the outside through the opening passage, so the operation of an air cushion on the deformation allowance space is avoided, and thus it is possible to effectively have elastic deformation of the hollow elastic body occur.

A fourth mode of the present invention provides the needleless connector according to the third mode, wherein a deformation constraint part is formed on the lid part so as to protrude inside the deformation allowance space and overlap an inner circumference surface of the peripheral wall of the hollow elastic body.

With the fourth mode, since the volume of elastic deformation of the peripheral wall of the hollow elastic body is constrained by the deformation constraint part provided on the lid part, it is possible to prevent bending or the like of the peripheral wall, and to further stabilize the deformation mode of the hollow elastic body. Because of that, during elastic deformation of the hollow elastic body, it is possible to avoid unintended constriction, closing or the like of the drug solution flow path, and to realize a stable communicating state of the drug solution flow path.

A fifth mode of the present invention provides the needleless connector according to the third or fourth mode, wherein a guide protrusion is provided on the lid part so as to protrude toward a center of a bottom part of the hollow elastic body, and a guide hole is provided at the center of the bottom part of the hollow elastic body such that the guide protrusion can be inserted in the guide hole.

With the fifth mode, during elastic deformation of the hollow elastic body, by the guide protrusion being inserted in the guide hole and sliding, a guide effect is exhibited in the insertion direction of the guide protrusion, and it is possible to prevent distorted deformation such as collapsing of hollow elastic body or the like. Because of that, it is possible to stabilize the deformation mode of the hollow elastic body, and to reliably switch between communicating and blocking of the drug solution flow path.

A sixth mode of the present invention provides the needleless connector according to any one of the third through fifth modes, wherein the lid part is integrally provided with the housing.

With the sixth mode, by using the housing, it is possible to provide a lid part with a small number of parts, and it is possible realize simplification of the structure and easier manufacturing.

A seventh mode of the present invention provides the needleless connector according to any one of the first through sixth modes, wherein a tapered surface whose diameter becomes smaller toward the inlet side of the drug solution flow path is provided on an outer circumference surface of the hollow elastic body, and a valve seat part is provided on the tapered surface so as to block the drug solution flow path by abutting the inner surface of the accommodation part of the housing.

With the seventh mode, the drug solution flow path is blocked not only by the elastic valve body, but also the valve seat part of the hollow elastic body, and since a double valve means is provided, leaking of drug solution, blood or the like to the inlet side from the drug solution flow path is more effectively prevented. Also, the valve seat part is provided by having at least a portion of the outer circumference surface of the hollow elastic body constituted by the tapered surface, and by the middle protrusion being pushed into the outlet side from the inlet side by the male luer, the blocking of the drug solution flow path by the valve seat part can be easily cancelled without requiring a special operation.

An eighth mode of the present invention provides the needleless connector according to any one of the first through seventh modes, wherein a concave groove is formed on the inner surface of the accommodation part of the housing so as to extend in a lengthwise direction of the drug solution flow path.

With the eighth mode, by the concave groove being provided on the inner circumference surface of the housing, even if the male luer is inserted and the peripheral wall of the hollow elastic body is deformed to the housing side, the drug solution flow path is stably ensured without having the drug solution flow path blocked by the hollow elastic body. Also, since the drug solution flow path is formed with the concave groove covered by the hollow elastic body by being installed on the accommodation part of the hollow elastic body, it is possible to very easily form the drug solution flow path in a designated shape. In fact, by having the bottom wall of the hollow elastic body elastically deform so as to enter inside the peripheral wall, since the covering of the opening of the concave groove by the bottom wall is cancelled, the inner circumference area of the accommodation part is opened by the opening of the concave groove, thus realizing expansion of the volume of the drug solution flow path.

Effect of the Invention

With the present invention, a hollow elastic body that is tube shaped having a bottom that faces toward the outlet side of the drug solution flow path is accommodated and arranged in the accommodation part of the housing, and by the distal end of the middle protrusion that protrudes toward the inlet side from the center part of the bottom wall of the hollow elastic body being pressed by the male luer, elastic deformation occurs such that the bottom wall of the hollow elastic body enters inside the peripheral wall. By doing this, during insertion of the male luer, the volume of the drug solution flow path extending between the housing and the hollow elastic body expands, making it possible to reliably realize a communicating state with the drug solution flow path, and when the male luer is removed, the volume of the drug solution flow path is reduced and positive pressure acts inside the drug solution flow path, so it is possible to realize a needleless connector for which backflow of blood does not occur easily.

EMBODIMENTS FOR CARRYING OUT THE INVENTION

Following, we will describe embodiments of the present invention while referring to drawings.

FIG. 1 through FIG. 5 show a needleless connector 10 as a first embodiment of the present invention. The needleless connector 10 has a constitution in which a housing 12 incorporates a disc valve 14 as an elastic valve body and a hollow elastic body 16. With the description hereafter, the vertical direction as a rule means the vertical direction in FIG. 5. Upward in FIG. 5 means the "inlet side of a drug solution flow path 80," and downward in FIG. 5 means the "outlet side of the drug solution flow path 80."

In more detail, the housing 12 is equipped with a base housing 18 and a cover housing 20 as an accommodation part. As shown in FIG. 6 to FIG. 9, the base housing 18 is an integrally molded component of a synthetic resin material, and a tubular part 22 and a peripheral wall part 24 which are respectively roughly cylindrical are provided coaxially separated by a designated distance in the radial direction, and the tubular part 22 and peripheral wall part 24 have a constitution joined by a roughly round disk shaped lid part 26 at the top end part.

The tubular part 22 exhibits a small diameter roughly cylindrical shape, and the outer circumference surface is constituted by a luer taper for which the diameter gradually shrinks facing downward. Also, a center hole 28 of the tubular part 22 is provided linearly in the vertical direction and opens at the lower surface of the tubular part 22, and the top end part reaches to the lid part 26.

The peripheral wall part 24 is a roughly cylindrical shape with a larger diameter than the tubular part 22, and is arranged enclosing the outer circumference side separated by a designated distance in relation to the tubular part 22. Also, a screw thread 30 is formed to protrude on the inner circumference surface on the peripheral wall part 24.

Also, an intravascular indwelling catheter (not illustrated) is connected to the proximal end opening part of the tubular part 22 of the base housing 18. With this embodiment, a female luer lock structure is constituted by the tubular part 22 and the peripheral wall part 24, making it possible to reliably connect and hold the intravascular indwelling catheter (not illustrated).

The lid part 26 has a roughly round disk shape, and is provided with a step surface 32 at the axial direction middle part, and the side lower than the step surface 32 is a large diameter part 34 with a diameter even larger than the peripheral wall part 24, and the side higher than the step surface 32 is a small diameter part 36. Then, the tubular part 22 protrudes downward from the center part of the large diameter part 34, and the peripheral wall part 24 protrudes downward from the outer circumference part of the large diameter part 34. As is clear from FIG. 5 as well, the lid part 26 of this embodiment is integrally provided with the housing 12 (base housing 18).

Figure 7:
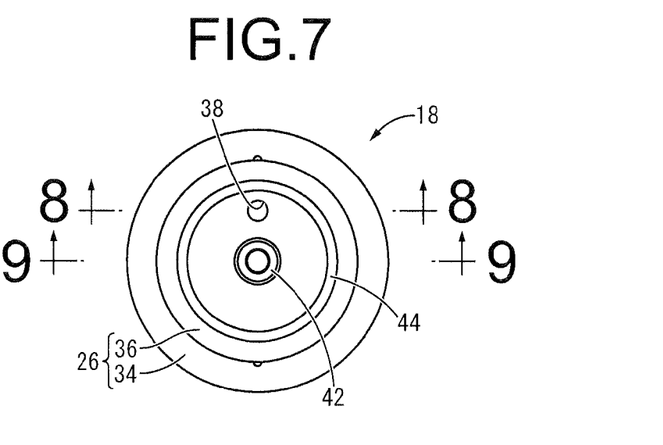
FIG. 7 is a plan view of the base housing shown in FIG. 6.
Figure 8:
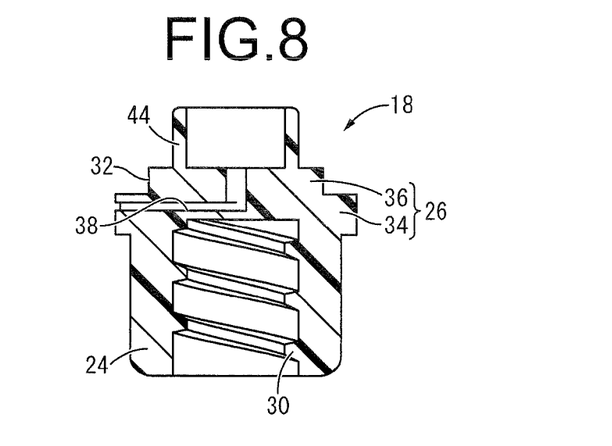
FIG. 8 is a cross section view taken along line 8-8 of FIG. 7.

An opening passage 38 is also formed on the lid part 26. As shown in FIG. 7 and FIG. 8, this opening passage 38 is a small diameter circular hole, wherein one end part opens to the top surface of the small diameter part 36, and extending at a curve midway, the other end part opens to the outer circumference surface of the large diameter part 34.

Figure 9:
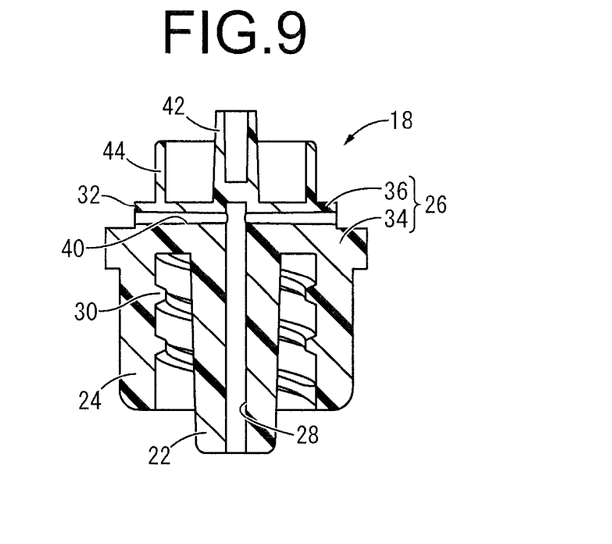
FIG. 9 is a cross section view taken along line 9-9 of FIG. 7.
Figure 10:
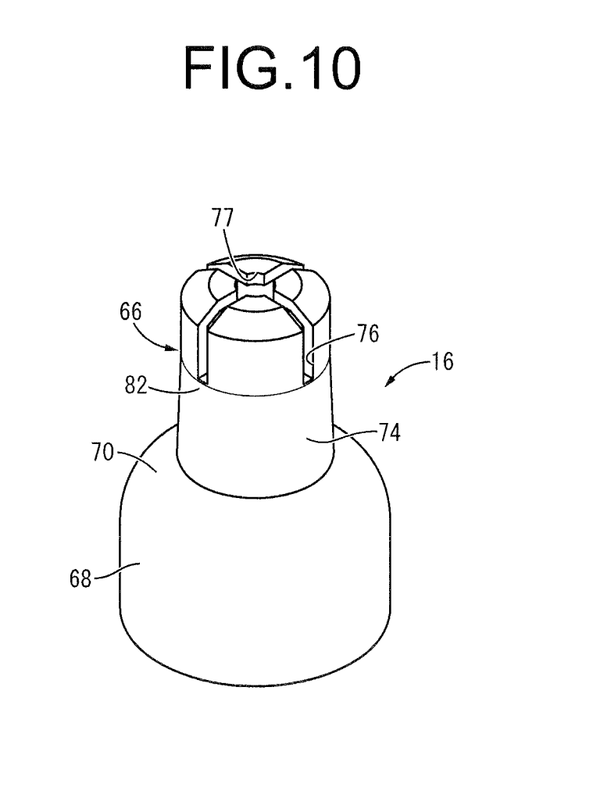
FIG. 10 is a perspective view of a hollow elastic body constituting the needleless connector shown in FIG. 1.
Figure 11:
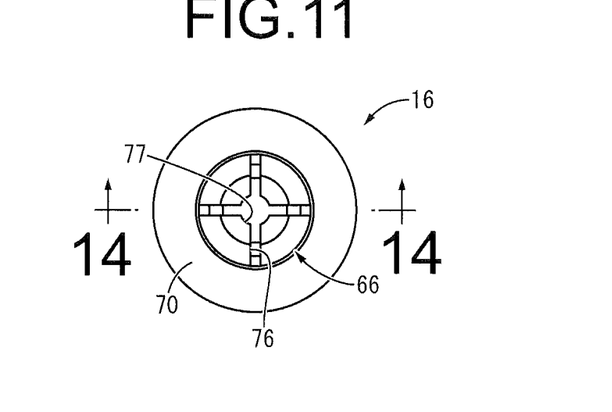
FIG. 11 is a plan view of the hollow elastic body shown in FIG. 10.
Figure 12:
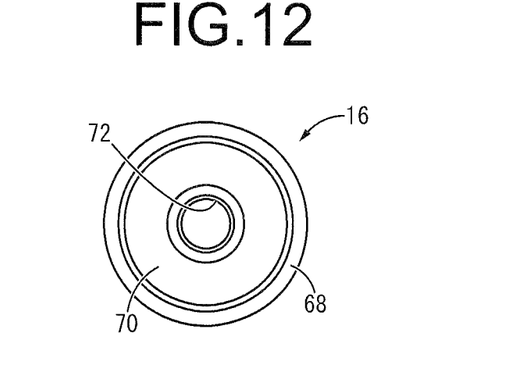
FIG. 12 is a bottom view of the hollow elastic body shown in FIG. 10.
Figure 13:
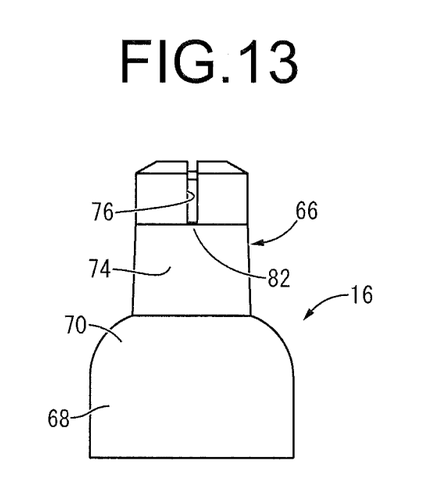
FIG. 13 is a front view of the hollow elastic body shown in FIG. 10.
Figure 14:
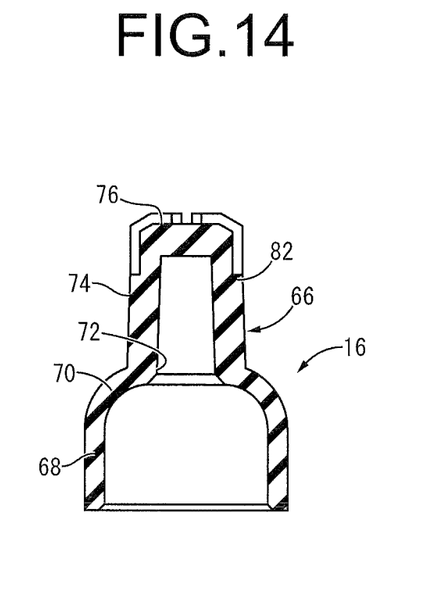
FIG. 14 is a cross section view taken along line 14-14 of FIG. 11.

Furthermore, as shown in FIG. 9, a communication hole 40 is formed piercing through in the axial perpendicular direction on the small diameter part 36 of the lid part 26, and both of its end parts open at the outer circumference surface of the small diameter part 36, and the center part of the lengthwise direction is in communication with the top end part of the center hole 28 formed on the tubular part 22. The communication hole 40 and center hole 28 and the opening passage 38 are provided independently without communicating with each other.

Furthermore, a guide protrusion 42 protruding upward is integrally formed at the radial direction center part of the small diameter part 36 on the lid part 26. This guide protrusion 42 has a roughly cylindrical shape with a bottom having a small diameter that opens facing upward, and the outer circumference surface has a tapered shape that gradually decreases in diameter facing upward.

Furthermore, on the lid part 26, a deformation constraint part 44 that protrudes upward is integrally formed at the radial direction middle part of the small diameter part 36. The deformation constraint part 44 has a roughly cylindrical shape with a larger diameter than the guide protrusion 42, and is provided separated by a designated distance at the outer circumference side of the guide protrusion 42. With the deformation constraint part 44, the outer circumference corner part of the protruding distal end has been chamfered, and the outer diameter dimension of the protruding distal end becomes gradually smaller toward the distal end side.

Meanwhile, the cover housing 20 has an overall roughly cylindrical shape, and has a step part 46 formed on the axial middle part, and the side lower than the step part 46 is used as a large diameter cover main unit 48, and the side higher than the step part 46 is used as a small diameter connection port part 50. Furthermore, the outer circumference surface of the upper part of the cover main unit 48 has a taper shape that gradually decreases in diameter facing upward. Also, the connection port part 50 constitutes a male luer lock by a screw thread 52 being formed to protrude on the outer circumference surface. The inner circumference surface of the cover housing 20 has a shape roughly corresponding to the outer circumference surface of the hollow elastic body 16 described later.

Furthermore, a lower communication groove 54 is formed as a concave groove on the cover main unit 48 of the cover housing 20. The lower communication groove 54 is a groove that opens at the inner circumference surface of the cover main unit 48, is formed with a roughly fixed depth dimension, and extends in the vertical direction. With this embodiment, four lower communication grooves 54 are formed at equal intervals on the circumference, but the number of lower communication grooves 54 is not particularly restricted.

Also, the base housing 18 is arranged so as to cover the lower opening part of the cover housing 20, the lower end surface of the cover housing 20 overlaps the large diameter part 34 of the base housing 18, and the housing 12 is formed by fixing these to each other using a fastening means such as adhesion, welding, screws or the like.

On this housing 12, an accommodation space 56 is formed using the inner circumference area of the cover housing 20, and this accommodation space 56 is put in communication with external space by opening upward through the upper opening part of the cover housing 20, and is put in communication with external space below through the communication hole 40 and the center hole 28 of the base housing 18. Two of the four lower communication grooves 54 are positioned in the circumference direction with the communication hole 40, and the lower communication groove 54 is in communication with the communication hole 40 at the lower end part. However, for example, if the lower end part of the lower communication groove 54 forms a ring shaped groove so as to be in communication with each other, and the lower communication groove 54 is made to be in communication with the communication hole 40 via this ring shaped groove, it is possible to make positioning of the base housing 18 and the cover housing 20 circumference direction unnecessary.

Figure 1:
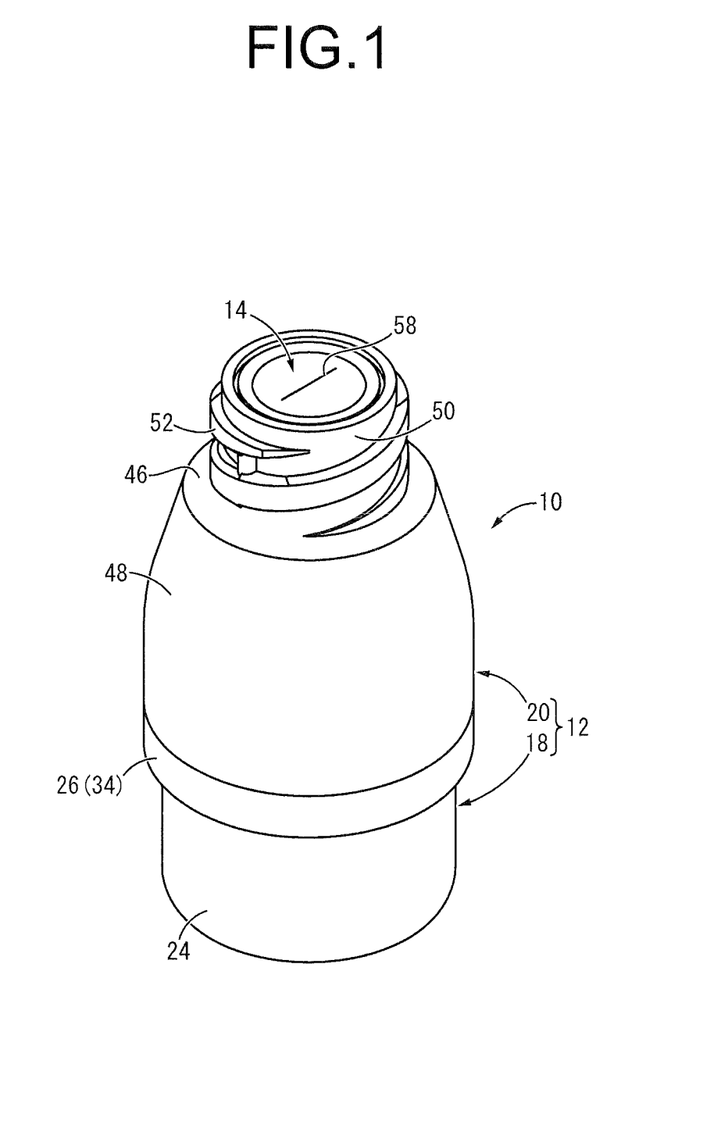
FIG. 1 is a perspective view showing a needleless connector as a first embodiment of the present invention.
Figure 2:
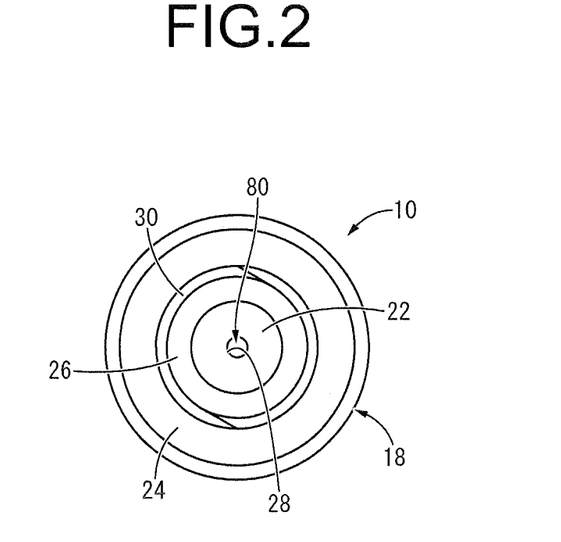
FIG. 2 is a bottom view of the needleless connector shown in FIG. 1.
Figure 3:
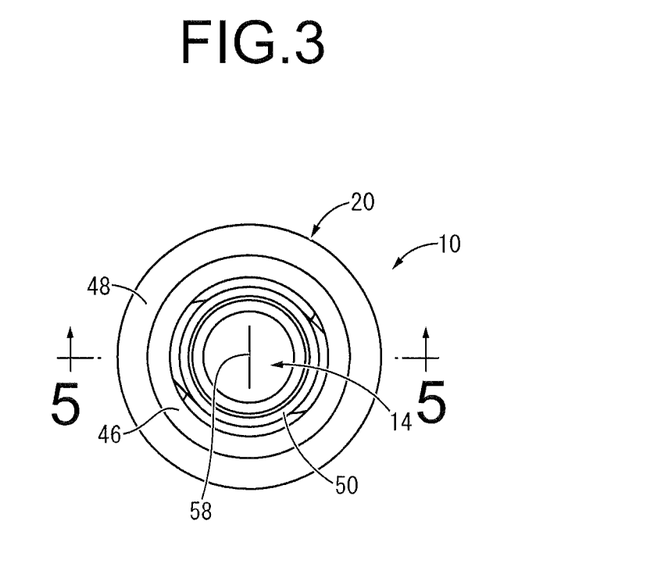
FIG. 3 is a plan view of the needleless connector shown in FIG. 1.
Figure 4:
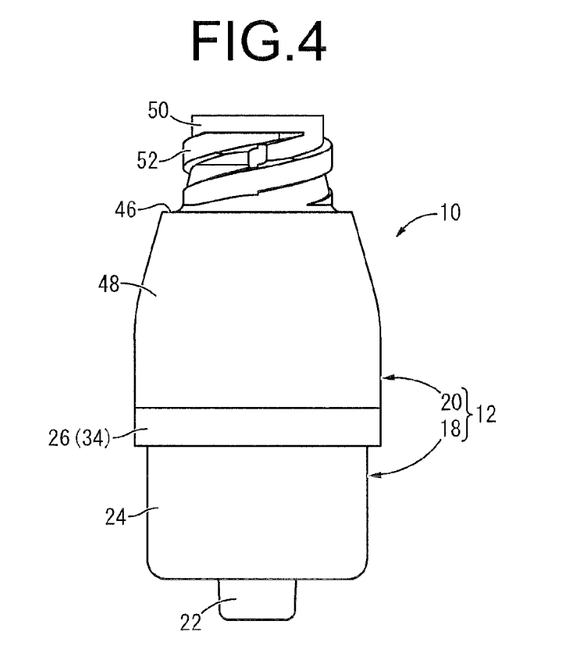
FIG. 4 is a front view of the needleless connector shown in FIG. 1.
Figure 5:
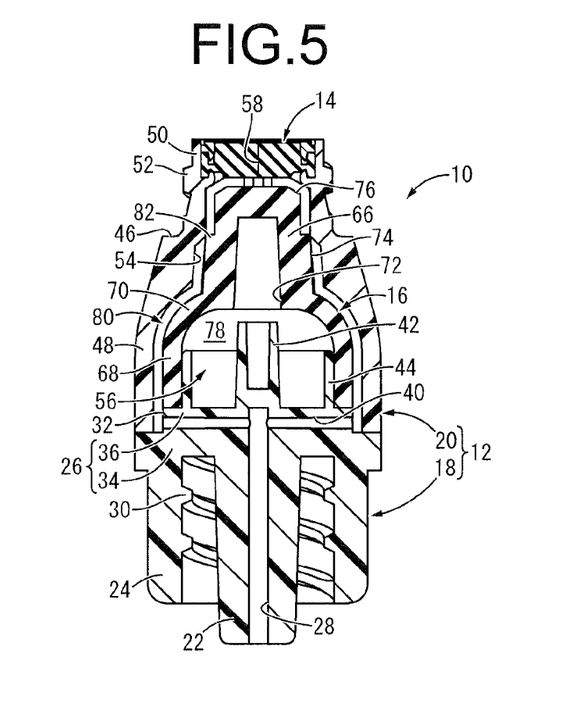
FIG. 5 is a cross section view taken along line 5-5 of FIG. 3.
Figure 6:
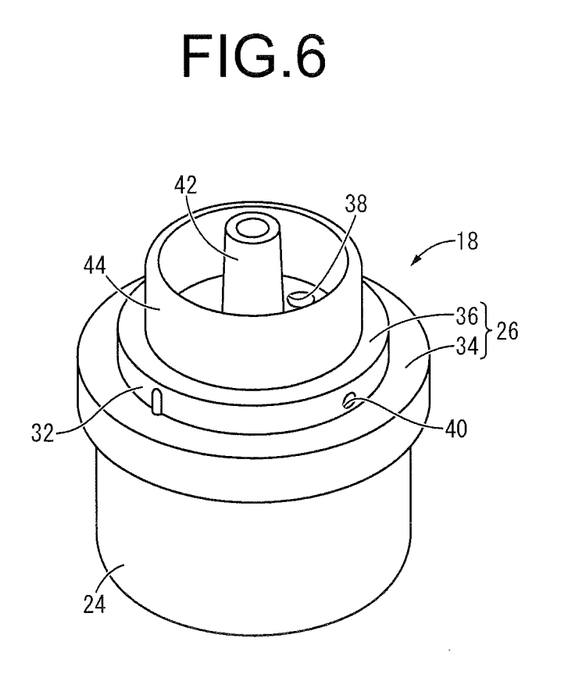
FIG. 6 is a perspective view of a base housing constituting the needleless connector shown in FIG. 1.

Also, a disc valve 14 is arranged on the upper end opening part of the connection port part 50 of the housing 12 (cover housing 20). The disc valve 14 is formed using a rubber elastic body exhibiting a roughly round disk shape, and as shown in FIG. 1 and FIG. 2, extends in one direction of the radial direction, and is equipped with a slit 58 that pierces through the thickness direction. Also, the disc valve 14 is inserted and held in the upper side opening part of the cover housing 20.

Also, the hollow elastic body 16 is accommodated in the accommodation space 56 provided under the disc valve 14, and is arranged on the inner circumference side of the cover housing 20. The hollow elastic body 16 is formed using an elastic material, and as shown in FIG. 10 to FIG. 14, has an inverted tube shape with a bottom that opens downward, and is an integrally molded component integrally equipped with a middle protrusion 66 protruding upward from the center part of its bottom wall (70).

In more detail, the hollow elastic body 16 is formed using an elastic material such as silicone rubber or the like, has a peripheral wall 68 and bottom wall 70 integrally formed, with the peripheral wall 68 having a roughly cylindrical shape, and the bottom wall 70 having a tapered shape that protrudes upward while it tilts toward the inner circumference side from the top end part of the peripheral wall 68. Also, a circular guide hole 72 is formed piercing in the thickness direction (vertical direction) on the radial direction center part of the bottom wall 70, and by having the diameter of this guide hole 72 be the same or larger than the maximum outer diameter dimension of the guide protrusion 42 provided on the base housing 18, the guide protrusion 42 can be inserted therein. The bottom wall 70 of this embodiment has a curved shape for which the tilt angle in relation to the axial direction in the vertical cross section becomes gradually larger facing upward.

The middle protrusion 66 has an inverted roughly cylindrical shape with a bottom that opens facing downward, and is integrally formed using an elastic material with the hollow elastic body 16, so as to protrude upward from the opening circumference edge part of the guide hole 72 on the bottom wall 70 of the hollow elastic body 16. In this way, by the hollow elastic body 16 being an integrally molded component integrally formed using an elastic material containing the middle protrusion 66, it is possible to reduce the number of parts and to simplify the structure.

Also, the middle protrusion 66 is made to be thicker than the bottom wall 70 and the peripheral wall 68 of the hollow elastic body 16, and by the push-in force by a male luer 86 described later being applied to the middle protrusion 66, deformation of the bottom wall 70 is made to occur with more priority than deformation of the middle protrusion 66.

Furthermore, the peripheral wall part of the middle protrusion 66 has a tapered shape for which the diameter gradually becomes larger facing the proximal end side (bottom side) of the peripheral wall part, and is constituted by a tapered surface 74 for which further below an upper communication groove 76 described later, with the outer circumference surface of the middle protrusion 66, the diameter becomes smaller toward the protruding distal end side. Also, the inner circumference area of the middle protrusion 66 has a tapered hole shape for which the diameter becomes gradually larger facing downward, opens downward through the guide hole 72 of the hollow elastic body 16, and constitutes a portion of the guide hole 72 of this embodiment.

Also, the upper communication groove 76 is formed at the top end part of the middle protrusion 66. The upper communication groove 76 opens at the top surface of the middle protrusion 66, exhibits a cross shaped extending in two directions of the radial direction, and reaches the outer circumference end part (see FIG. 11), extends linearly facing downward in the axial direction from the outer circumference end part and opens at the outer circumference surface of the top end part of the middle protrusion 66 (see FIG. 13). With this embodiment, a circular recess 77 is formed open at the radial direction center part of the top surface of the middle protrusion 66, and this recess 77 is in communication with the upper communication groove 76.

The hollow elastic body 16 constituted in this way is accommodated and arranged in the accommodation space 56 of the housing 12. Specifically, the hollow elastic body 16 is arranged between the base housing 18 and the disc valve 14 facing opposite in the axial direction, and the opening part facing downward is covered by the lid part 26 of the base housing 18. Also, a deformation allowance space 78 is formed between the hollow elastic body 16 and the lid part 26 of the base housing 18, and this deformation allowance space 78 is put in communication with the external space through the opening passage 38 of the lid part 26.

Furthermore, the deformation constraint part 44 of the base housing 18 is inserted from the lower side opening part of the hollow elastic body 16, is overlapped on the inner circumference surface of the peripheral wall 68, and the peripheral wall 68 of the hollow elastic body 16 is sandwiched between the deformation constraint part 44 and the cover housing 20. In the state with the hollow elastic body 16 arranged in the accommodation space 56, the guide protrusion 42 of the base housing 18 is positioned lower than the bottom surface of the bottom wall 70 of the hollow elastic body 16, protruding toward the center part of the bottom wall 70, and is positioned in the axial perpendicular direction in relation to the guide hole 72 of the hollow elastic body 16 and arranged with a separation downward.

Also, by the hollow elastic body 16 being arranged in the accommodation space 56, the outer circumference surface of the hollow elastic body 16 is tightly adhered without a gap to the inner circumference surface of the cover housing 20, or is overlapped with a small gap at a level for which there is no problem of leaking or residue of the drug solution or the like. By doing this, the opening part of the lower communication groove 54 formed on the cover housing 20 is covered by the hollow elastic body 16, and a tunnel shaped flow path is formed between the cover housing 20 and the hollow elastic body 16. By that tunnel shaped flow path being in communication with the communication hole 40 and the center hole 28 of the base housing 18, at least at a portion (the part constituted by the lower communication groove 54), the drug solution flow path 80 is formed extending between the housing 12 and the hollow elastic body 16. In this way, if the lower communication groove 54 opens on the inner circumference surface of the cover housing 20, by arranging the hollow elastic body 16, it is possible to easily form the drug solution flow path 80 between the housing 12 and the hollow elastic body 16.

Furthermore, by the outer circumference surface of the hollow elastic body 16 overlapping the inner circumference surface of the cover housing 20, the opening part of the upper communication groove 76 formed on the middle protrusion 66 is covered by the cover housing 20, and a tunnel form flow path is formed between the cover housing 20 and the hollow elastic body 16.

Also, the top end part of the lower communication groove 54 does not reach as far as the lower end part of the upper communication groove 76 and is positioned separated downward, and a valve seat part 82 constituted by the lower wall part of the upper communication groove 76 on the middle protrusion 66 abuts the upper wall part of the lower communication groove 54 on the cover housing 20. By doing this, the lower communication groove 54 and the upper communication groove 76 are separated by the valve seat part 82, and the drug solution flow path 80 is blocked at the middle part in the flow path longitudinal direction by the valve seat part 82.

The needleless connector 10 constituted in this way is used with a catheter or the like connected to the proximal end opening part of the drug solution flow path 80 as described previously. Also, under those use conditions, as shown in FIG. 15, by a male luer 86 such as a syringe 84 or the like being pushed in from the connection port part 50 of the housing 12 from above, the slit 58 of the disc valve 14 is opened.

Figure 15:
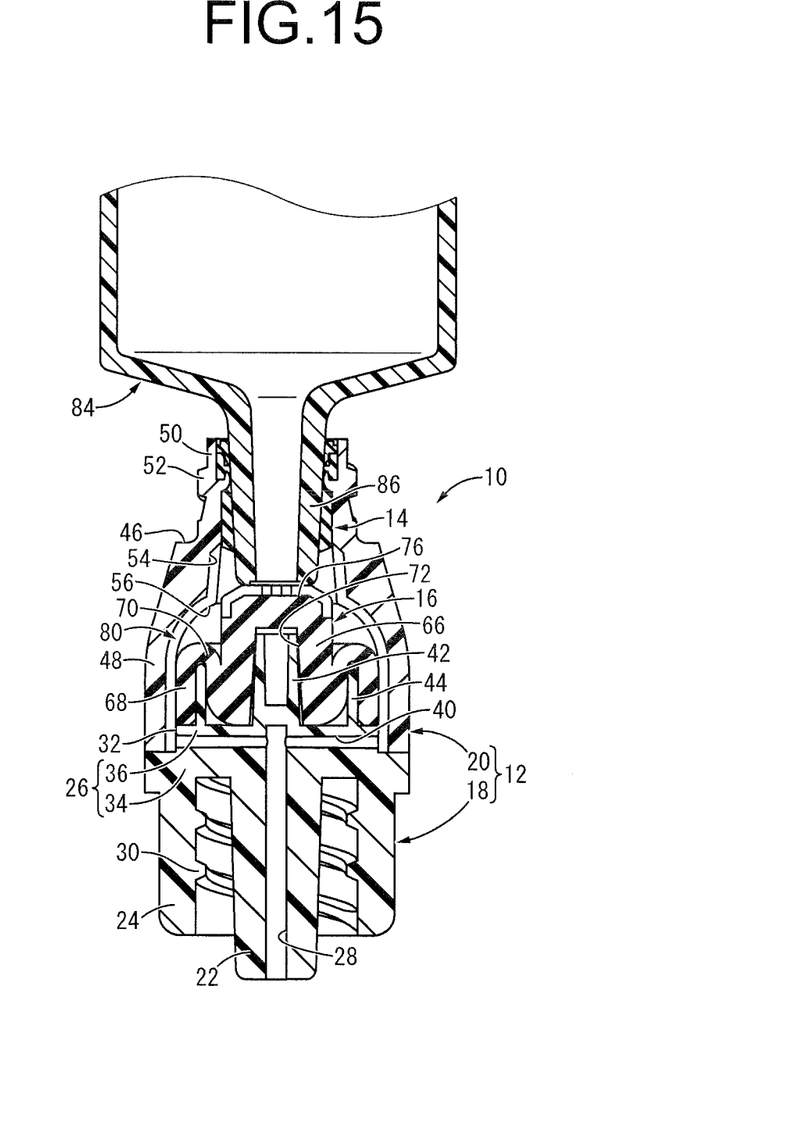
FIG. 15 is a vertical cross section view showing the needleless connector shown in FIG. 1, showing the communication state of a drug solution flow path.

The male luer 86 of the syringe 84 shown in FIG. 15 is a male luer lock structure, and the connected state to the connection port part 50 of the cover housing 20 is reliably maintained. This male luer 86 can be not only a fixed luer lock structure, but also a luer slip structure that is fixed by being pushed in.

Here, with the needleless connector 10, when the male luer 86 is inserted in the slit 58, the push-in force of the male luer 86 is applied to the hollow elastic body 16, and by the blocking of the upper and lower communication grooves 76 and 54 by the valve seat part 82 being cancelled, the male luer 86 is in a communicating state with the drug solution flow path 80.

In more specific terms, by the male luer 86 inserted piercing through the slit 58 of the disc valve 14 pushing the middle protrusion 66 of the hollow elastic body 16 downward, the middle protrusion 66 is displaced downward, and the abutting between the valve seat part 82 of the middle protrusion 66 and the inner circumference surface of the housing 12 is cancelled. By doing this, the lower communication groove 54 and the upper communication groove 76 are in communication with each other, and the male luer 86 is put in communication with the drug solution flow path 80. In this way, the drug solution flow path 80 has the housing 12 provided so as to pierce through vertically which is the lengthwise direction, and its inlet is used as the slit 58 of the disc valve 14 arranged at the top end part of the housing 12, and the outlet is used as the center hole 28 of the tubular part 22 provided at the bottom end part of the housing 12.

In light of that, by the middle protrusion 66 being pressed downward by the male luer 86, the inner circumference part of the bottom wall 70 of the hollow elastic body 16 is pressed downward. In accordance with this downward pressing, with the hollow elastic body 16, the inner circumference part of the bottom wall 70 is elastically deformed so as to enter the inner circumference side (inside the deformation allowance space 78) of the peripheral wall 68. By doing this, the bottom wall 70 of the hollow elastic body 16 is separated from the inner circumference surface of the cover housing 20, and the volume of the drug solution flow path 80 formed between the housing 12 and the hollow elastic body 16 actively increases. Because of that, when the male luer 86 is removed, positive pressure is generated in the drug solution flow path 80 of the needleless connector 10, and an effect of preventing backflow of blood or the like is exhibited.

In other words, the accommodation space 56 is divided into the inner circumference side deformation allowance space 78 and the outer circumference side drug solution flow path 80 sandwiching the hollow elastic body 16, and the volume ratio of the deformation allowance space 78 and the drug solution flow path 80 is made to change by the push-in force of the male luer 86 acting to cause elastic deformation of the hollow elastic body 16. Also, when the drug solution flow path 80 is in communication, by the bottom wall 70 entering inside the peripheral wall 68, the volume of the deformation allowance space 78 is reduced, and the volume of the drug solution flow path 80 is increased. On the other hand, when the drug solution flow path 80 is blocked, by the bottom wall 70 going to the outside from inside the peripheral wall 68, the capacity of the deformation allowance space 78 is increased, and the volume of the drug solution flow path 80 is reduced, so positive pressure is generated in the drug solution flow path 80.

Particularly with the needleless connector 10 of this embodiment, the peripheral wall 68 of the hollow elastic body 16 is sandwiched between the cover housing 20 and the deformation constraint part 44 of the base housing 18, and deformation is restricted. Because of that, when the middle protrusion 66 is pushed by the male luer 86, there is now swelling deformation to the outside by the hollow elastic body 16, and elastic deformation is done stably so as to have the bottom wall 70 enter the peripheral wall 68, so the drug solution flow path 80 switches to the communicating state with high reliability, and the backflow prevention effect is reliably exhibited using the volume change of the drug solution flow path 80.

Also, the outer circumference surface of the hollow elastic body 16 has a shape roughly corresponding to the inner circumference surface of the cover housing 20, and the outer circumference surface of the hollow elastic body 16 and inner circumference surface of the cover housing 20 are overlapped at the part with the upper and lower communication grooves 76 and 54 removed via no gap or a tiny gap. Because of that, by the hollow elastic body 16 recovering its initial state from the deformed state by removal of the male luer 86, it is pushed to the outlet side without drug solution or the like remaining between the cover housing 20 and the hollow elastic body 16, and it is possible to reliably send to the outlet side the target volume of drug solution or the like.

Furthermore, the upper and lower communication grooves 76 and 54 that constitute the drug solution flow path 80 extend in the vertical direction across a broad area excluding a portion of the upper communication groove 76, so the drug solution or the like inside the drug solution flow path 80 is automatically led to the outlet side by gravitational action, and is exhausted to outside from the outlet (center hole 28). In this way, having drug solution remain inside the drug solution flow path 80 is also prevented by the shape of the drug solution flow path 80 (extension direction).

Furthermore, by the middle protrusion 66 being pressed by the male luer 86, the guide protrusion 42 provided on the base housing 18 is made to be inserted in the guide hole 72 formed on the bottom wall 70 of the hollow elastic body 16. By doing this, distorted deformation such as deformation by which the middle protrusion 66 collapses or the like is prevented, and since the hollow elastic body 16 stably elastically deforms in the target deformation mode, switching to the communicating state of the drug solution flow path 80 and action for preventing backflow of blood or the like are both realized stably.

In particular with this embodiment, the guide hole 72 has a tapered shape for which the diameter expands facing the opening side, and the guide protrusion 42 has a tapered shape by which the diameter decreases facing the protruding distal end side. By doing this, the guide protrusion 42 is reliably inserted in the guide hole 72, guiding action by insertion of the guide protrusion 42 in the guide hole 72 is reliably exhibited, and the form after elastic deformation of the hollow elastic body 16 is stabilized.

Also, in addition to using the disc valve 14 to switch between the male luer 86 and the drug solution flow path 80 being connected and cancelled, the drug solution flow path 80 is also made to be blocked by the valve seat part 82 of the hollow elastic body 16 abutting the inner circumference surface of the housing 12. Since a double valve means is provided in this way, leaking of drug solution, blood or the like to the inlet side is effectively prevented.

Above, we gave a detailed description of embodiments of the present invention, but the present invention is not limited to that specific description. For example, the shape of the hollow elastic body is not to be interpreted in limiting fashion by the specific shape shown with the aforementioned embodiments. In specific terms, for example, the shape of the bottom wall, in addition to being a shape having a curved cross section as shown in the embodiments noted above, can also be a plane shape that broadens in the axial perpendicular direction, or can be a tapered shape tilted at a roughly fixed tilt angle or the like.

Furthermore, the valve seat part can also be provided on the bottom wall 70 rather than on the middle protrusion 66, or can also not be provided. It is also possible to provide a plurality of valve seat parts to further improve the blocking performance of the drug solution flow path 80.

Furthermore, the middle protrusion is not limited to being an item that has a hollow form as shown with the embodiments noted above, and can also be a solid pillar shape. In this case, with the embodiments noted above, the guide protrusion 42 provided on the base housing 18 is an item having a small protrusion height correlating to the thickness of the bottom wall 70 of the hollow elastic body 16, or with that omitted.

It is also possible to make the thickness of the bottom wall of the hollow elastic body smaller than the thickness of the peripheral wall. By working in this way, since elastic deformation occurs easily with the hollow elastic body at the bottom wall part, when inserting the male luer, elastic deformation of the bottom wall so as to enter the peripheral wall inner circumference side is realized reliably.

Also, with the embodiments noted above, the lid part 26 is integrally provided with the base housing 18, but the lid part can also be constituted as a separate member from the housing.

Furthermore, the middle protrusion can also be formed as a separated unit from the hollow elastic body, and in that case, the middle protrusion and the hollow elastic body can be fixed later using a means such as adhesion, welding or the like. The middle protrusion does not absolutely have to be formed using an elastic material, and for example can also be formed using a hard synthetic resin or the like.

Also, as shown by example with the embodiments noted above as well, the drug solution flow path 80 can be formed by the concave groove formed at one or both of the cover housing 20 inner circumference surface and the hollow elastic body 16 and middle protrusion 66 outer circumference surface being covered.

Also, with the embodiments noted above, the hollow elastic body is formed using silicone rubber, but as long as it is an item that follows the gist of the present invention, the material doesn't matter. Preferably, silicone rubber, synthetic rubber, natural rubber, a thermoplastic elastomer or the like is used.

Also, with the embodiments noted above, the hollow elastic body was a constitution for which the middle protrusion is pressed downward by the male luer, but for example, it is also possible to be a constitution for which a plunger is provided separately between the male luer and the hollow body and arrange it to be movable within the housing, and by that plunger that is moved by the male luer, to have the middle protrusion of the hollow elastic body undergo pressing deformation.

KEYS TO SYMBOLS

10: Needleless connector
12: Housing
14: Disc valve (elastic valve body)

16: Hollow elastic body
20: Cover housing (accommodation part)
26: Lid part
28: Center hole (outlet)
38: Opening passage
42: Guide protrusion
44: Deformation constraint part
54: Lower communication groove (concave groove)
58: Slit (inlet)
66: Middle protrusion
68: Peripheral wall
70: Bottom wall
72: Guide hole
74: Tapered surface
76: Upper communication groove
78: Deformation allowance space
80: Drug solution flow path
82: Valve seat part
86: Male luer

The invention claimed is:

1. A needleless connector comprising:
a housing;
an inlet and an outlet of a drug solution flow path being respectively provided at one side and another side of a lengthwise direction of the housing;
an elastic valve body having a slit being attached to the inlet of the drug solution flow path of the housing such that the drug solution flow path is switched from a blocked state to a communicating state by opening the slit by the elastic valve body being deformed by means of insertion of a male luer from the inlet of the drug solution flow path;
a hollow elastic body having a tube shape with a bottom that opens toward an outlet side of the drug solution flow path being accommodated and arranged in an accommodation part formed on the housing;
a middle protrusion being provided protruding toward an inlet side of the drug solution flow path from a center part of a bottom wall of the hollow elastic body; and
a deformation allowance space provided inside the hollow elastic body so as to allow elastic deformation of the hollow elastic body, wherein
by means of insertion of the male luer, the bottom wall of the hollow elastic body undergoes the elastic deformation so as to enter inside a peripheral wall of the hollow elastic body, and a volume of the drug solution flow path formed between an outer surface of the hollow elastic body and an inner surface of the housing is increased,
by means of removal of the male luer, the elastic deformation of the hollow elastic body is cancelled, and the volume of the drug solution flow path is reduced, and
the drug solution flow path is not in communication with the deformation allowance space.

2. The needleless connector according to claim 1, wherein the hollow elastic body is an integrally molded component that is integrally molded using an elastic material including the middle protrusion.

3. The needleless connector according to claim 1, further comprising a lid part that covers an opening of the hollow elastic body, so that the deformation allowance space is defined between the lid part and an inner surface of the hollow elastic body, and an opening passage being formed on the lid part so as to put the deformation allowance space in communication with an external space.

4. The needleless connector according to claim 3, further comprising a deformation constraint part being formed on the lid part so as to protrude inside the deformation allowance space and overlap an inner circumference surface of the peripheral wall of the hollow elastic body.

5. The needleless connector according to claim 3, further comprising a guide protrusion being provided on the lid part so as to protrude toward a center of a bottom part of the hollow elastic body, and a guide hole being provided at the center of the bottom part of the hollow elastic body such that the guide protrusion can be inserted in the guide hole.

6. The needleless connector according to claim 3, wherein the lid part is integrally provided with the housing.

7. The needleless connector according to claim 1, further comprising a tapered surface whose diameter becomes smaller toward the inlet side of the drug solution flow path being provided on an outer circumference surface of the hollow elastic body, and a valve seat part being provided on the tapered surface so as to block the drug solution flow path by abutting the inner surface of the accommodation part of the housing.

8. The needleless connector according to claim 1, further comprising a concave groove being formed on the inner surface of the accommodation part of the housing so as to extend in a lengthwise direction of the drug solution flow path.

9. The needleless connector according to claim 1, wherein the middle protrusion is made to be thicker than the bottom wall and the peripheral wall of the hollow elastic body.

10. A hollow elastic body for a needleless connector, assembled in a state accommodated in a housing provided with an inlet and an outlet of a drug solution flow path at one side and another side of a lengthwise direction thereof, respectively, wherein
the hollow elastic body has a tube shape with a bottom equipped with a bottom wall and a peripheral wall such that the hollow elastic body is accommodated and arranged in the housing in a state opened toward an outlet side of the drug solution flow path so as to form the drug solution flow path between an outer surface of the hollow elastic body and an inner surface of the housing,
the hollow elastic body includes a middle protrusion being provided protruding toward an inlet side of the drug solution flow path from a center part of the bottom wall and a deformation allowance space provided inside the hollow elastic body so as to allow elastic deformation of the hollow elastic body,
by means of insertion of a male luer from the inlet side, the bottom wall undergoes the elastic deformation so as to enter inside the peripheral wall, and a volume of the drug solution flow path formed between the outer surface of the hollow elastic body and the inner surface of the housing is increased,
by means of removal of the male luer, the elastic deformation is cancelled, and the volume of the drug solution flow path is reduced, and
the drug solution flow path is not in communication with the deformation allowance space.

11. The hollow elastic body according to claim 10, wherein the middle protrusion is made to be thicker than the bottom wall and the peripheral wall of the hollow elastic body.

12. A needleless connector comprising:
a housing;
an inlet and an outlet of a drug solution flow path being respectively provided at one side and another side of a lengthwise direction of the housing; and
a hollow elastic body being assembled in a state accommodated in the housing, wherein
the hollow elastic body has a tube shape with a bottom equipped with a bottom wall and a peripheral wall such that the hollow elastic body is accommodated and arranged in the housing in a state opened toward an outlet side of the drug solution flow path so as to form the drug solution flow path between an outer surface of the hollow elastic body and an inner surface of the housing, the hollow elastic body includes a middle protrusion being provided protruding toward an inlet side of the drug solution flow path from a center part of the bottom wall and a deformation allowance space provided inside the hollow elastic body so as to allow elastic deformation of the hollow elastic body, by means of insertion of a male luer from the inlet side, the bottom wall undergoes the elastic deformation so as to enter inside the peripheral wall, and a volume of the drug solution flow path formed between the outer surface of the hollow elastic body and the inner surface of the housing is increased, by means of removal of the male luer, the elastic deformation is cancelled, and the volume of the drug solution flow path is reduced, and the drug solution flow path is not in communication with the deformation allowance space.

13. The needleless connector according to claim 12, wherein the middle protrusion is made to be thicker than the bottom wall and the peripheral wall of the hollow elastic body.

* * * * *